(12) United States Patent
Ortiz et al.

(10) Patent No.: US 7,914,551 B2
(45) Date of Patent: *Mar. 29, 2011

(54) ELECTROACTIVE POLYMER-BASED ARTICULATION MECHANISM FOR MULTI-FIRE SURGICAL FASTENING INSTRUMENT

(75) Inventors: Mark Ortiz, Milford, OH (US); Frederick Shelton, IV, Hillsboro, OH (US); Joseph Hueil, Loveland, OH (US); Jeffrey Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 994 days.

This patent is subject to a terminal disclaimer.

(21) Appl. No.: 11/162,984

(22) Filed: Sep. 30, 2005

(65) Prior Publication Data

US 2006/0047305 A1 Mar. 2, 2006

Related U.S. Application Data

(63) Continuation-in-part of application No. 11/082,495, filed on Mar. 17, 2005, now Pat. No. 7,506,790.

(60) Provisional application No. 60/591,694, filed on Jul. 28, 2004.

(51) Int. Cl.
*A61B 17/04* (2006.01)
(52) U.S. Cl. .................. 606/205; 606/207; 227/175.1
(58) Field of Classification Search ............... 227/175.1, 227/180.1, 19; 606/205, 206
See application file for complete search history.

(56) References Cited

U.S. PATENT DOCUMENTS

| | | | |
|---|---|---|---|
| 4,473,077 A | 9/1984 | Noiles et al. | |
| 4,543,090 A | 9/1985 | McCoy | |
| 4,554,064 A | 11/1985 | McClintock et al. | |
| 4,601,705 A | 7/1986 | McCoy | |
| 4,753,223 A | 6/1988 | Bremer | |
| 4,892,545 A | 1/1990 | Day et al. | |
| 5,171,249 A | 12/1992 | Stefanchik et al. | |
| 5,290,240 A | 3/1994 | Horres, Jr. | |
| 5,312,023 A * | 5/1994 | Green et al. | 227/175.1 |
| 5,330,087 A | 7/1994 | Murray et al. | |
| 5,372,124 A | 12/1994 | Takayama et al. | |
| 5,387,194 A | 2/1995 | Williams et al. | |

(Continued)

FOREIGN PATENT DOCUMENTS

DE 4015562 A1 11/1991

(Continued)

OTHER PUBLICATIONS

Dec. 5, 2008 Office Action for U.S. Appl. No. 11/162,991.

(Continued)

*Primary Examiner* — Todd E Manahan
*Assistant Examiner* — Michael G Mendoza

(57) ABSTRACT

Methods and devices are provided for effecting movement of one or more components of a multifire device, such as a clip applier, hernia tacker, or skin stapler. In one exemplary embodiment, a surgical fastening instrument is provided having an elongate shaft with an end effector coupled thereto and adapted to apply one or more surgical fasteners to tissue. An electrically expandable and contractible actuator, such as an electroactive polymer actuator, can be used to drive a fastener advancing or forming assembly through the elongate shaft, thereby driving a surgical fastener into tissue. In another embodiment, an electrically expandable and contractible actuator, such as an electroactive polymer actuator, can be used to effect movement of an articulation joint formed between the elongate shaft and the end effector.

10 Claims, 16 Drawing Sheets

U.S. PATENT DOCUMENTS

| | | |
|---|---|---|
| 5,389,098 A | 2/1995 | Tsuruta et al. |
| 5,397,046 A | 3/1995 | Savage et al. |
| 5,397,324 A | 3/1995 | Carroll et al. |
| 5,399,256 A | 3/1995 | Bohs et al. |
| 5,403,312 A | 4/1995 | Yates et al. |
| 5,413,267 A | 5/1995 | Solyntjes et al. |
| 5,413,268 A | 5/1995 | Green et al. |
| 5,431,668 A | 7/1995 | Burbank, III et al. |
| 5,441,193 A | 8/1995 | Gravener |
| 5,445,304 A | 8/1995 | Plyley et al. |
| 5,465,895 A | 11/1995 | Knodel et al. |
| 5,468,250 A | 11/1995 | Paraschac et al. |
| 5,484,095 A | 1/1996 | Green et al. |
| 5,503,638 A | 4/1996 | Cooper et al. |
| 5,520,787 A | 5/1996 | Hanagan et al. |
| 5,535,937 A | 7/1996 | Boiarski et al. |
| 5,542,594 A | 8/1996 | McKean et al. |
| 5,549,628 A | 8/1996 | Cooper et al. |
| 5,555,555 A | 9/1996 | Sato et al. |
| 5,562,239 A | 10/1996 | Boiarski et al. |
| 5,584,425 A | 12/1996 | Savage et al. |
| 5,592,668 A | 1/1997 | Harding et al. |
| 5,599,329 A | 2/1997 | Gabbay |
| 5,601,582 A | 2/1997 | Shelton et al. |
| 5,609,285 A | 3/1997 | Grant et al. |
| 5,624,452 A | 4/1997 | Yates |
| 5,634,584 A | 6/1997 | Okorocha et al. |
| 5,653,721 A | 8/1997 | Knodel et al. |
| 5,661,887 A | 9/1997 | Byrne et al. |
| 5,665,285 A | 9/1997 | Hattori et al. |
| 5,667,517 A | 9/1997 | Hooven |
| 5,669,918 A | 9/1997 | Balazs et al. |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,409 A | 12/1997 | Rayburn et al. |
| 5,704,534 A | 1/1998 | Huitema et al. |
| 5,709,334 A | 1/1998 | Sorrentino et al. |
| 5,735,445 A | 4/1998 | Vidal et al. |
| 5,769,892 A | 6/1998 | Kingwell |
| 5,779,130 A | 7/1998 | Alesi et al. |
| 5,792,165 A | 8/1998 | Klieman et al. |
| 5,797,537 A | 8/1998 | Oberlin et al. |
| 5,810,855 A | 9/1998 | Rayburn et al. |
| 5,826,776 A | 10/1998 | Schulze et al. |
| 5,829,662 A | 11/1998 | Allen et al. |
| 5,855,565 A | 1/1999 | Bar-Cohen et al. |
| 5,865,361 A | 2/1999 | Milliman et al. |
| 5,868,744 A | 2/1999 | Willmen |
| 5,876,401 A | 3/1999 | Schulze et al. |
| 5,901,895 A | 5/1999 | Heaton et al. |
| 5,902,312 A | 5/1999 | Frater et al. |
| 5,908,427 A | 6/1999 | McKean et al. |
| 5,918,791 A | 7/1999 | Sorrentino et al. |
| 5,959,852 A | 9/1999 | Deloy et al. |
| 5,964,774 A | 10/1999 | McKean et al. |
| 5,972,165 A | 10/1999 | Sethna et al. |
| 6,010,054 A | 1/2000 | Johnson et al. |
| 6,032,849 A | 3/2000 | Mastri et al. |
| 6,033,427 A | 3/2000 | Lee |
| 6,063,097 A | 5/2000 | Oi et al. |
| 6,079,606 A | 6/2000 | Milliman et al. |
| 6,109,500 A | 8/2000 | Alli et al. |
| 6,202,914 B1 | 3/2001 | Geiste et al. |
| 6,241,139 B1 | 6/2001 | Milliman et al. |
| 6,302,311 B1 | 10/2001 | Adams et al. |
| 6,330,965 B1 | 12/2001 | Milliman et al. |
| 6,488,197 B1 | 12/2002 | Whitman |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,514,237 B1 | 2/2003 | Maseda |
| 6,545,384 B1 | 4/2003 | Pelrine et al. |
| 6,577,899 B2 | 6/2003 | Lebel et al. |
| 6,583,533 B2 | 6/2003 | Pelrine et al. |
| 6,586,859 B2 | 7/2003 | Kornbluh et al. |
| 6,595,852 B2 | 7/2003 | Wang |
| 6,652,521 B2 | 11/2003 | Schulze |
| 6,656,193 B2 | 12/2003 | Grant et al. |
| 6,667,825 B2 | 12/2003 | Lu et al. |
| 6,669,073 B2 | 12/2003 | Milliman et al. |
| 6,699,245 B2 | 3/2004 | Dinger et al. |
| 6,716,233 B1 | 4/2004 | Whitman |
| 6,740,079 B1 | 5/2004 | Eggers et al. |
| 6,770,027 B2 | 8/2004 | Banik et al. |
| 6,786,382 B1 | 9/2004 | Hoffman |
| 6,830,174 B2 | 12/2004 | Hillstead et al. |
| 6,835,173 B2 | 12/2004 | Couvillon, Jr. |
| 6,840,246 B2 | 1/2005 | Downing |
| 6,905,057 B2 | 6/2005 | Swayze et al. |
| 6,913,579 B2 | 7/2005 | Truckai et al. |
| 6,923,804 B2 | 8/2005 | Eggers et al. |
| 6,959,852 B2 | 11/2005 | Shelton, IV et al. |
| 6,964,363 B2 | 11/2005 | Wales et al. |
| 6,969,395 B2 | 11/2005 | Eskuri |
| 6,978,921 B2 | 12/2005 | Shelton, IV et al. |
| 6,981,628 B2 | 1/2006 | Wales |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,063,699 B2 | 6/2006 | Hess et al. |
| 7,074,217 B2 | 7/2006 | Strul et al. |
| 7,083,075 B2 | 8/2006 | Swayze et al. |
| 7,111,769 B2 | 9/2006 | Wales et al. |
| 7,140,528 B2 | 11/2006 | Shelton, IV |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,208,005 B2 | 4/2007 | Frecker et al. |
| 7,213,736 B2 | 5/2007 | Wales et al. |
| 7,238,195 B2 | 7/2007 | Viola |
| 7,320,700 B2 | 1/2008 | Cooper et al. |
| 7,338,509 B2 | 3/2008 | Mattison |
| 7,354,447 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,509 B2 | 7/2008 | Ortiz et al. |
| 7,407,074 B2 | 8/2008 | Ortiz et al. |
| 7,431,730 B2 | 10/2008 | Viola |
| 7,487,899 B2 | 2/2009 | Shelton, IV et al. |
| 7,506,790 B2 | 3/2009 | Shelton, IV |
| 7,513,408 B2 | 4/2009 | Shelton, IV et al. |
| 7,517,356 B2 | 4/2009 | Heinrich |
| 7,559,452 B2 | 7/2009 | Wales et al. |
| 7,607,557 B2 | 10/2009 | Shelton, IV et al. |
| 7,641,093 B2 | 1/2010 | Doll et al. |
| 2001/0029384 A1 | 10/2001 | Nicholas et al. |
| 2002/0074005 A1 | 6/2002 | Hogg et al. |
| 2002/0108112 A1 | 8/2002 | Wallace et al. |
| 2002/0165541 A1 | 11/2002 | Whitman |
| 2003/0065358 A1 | 4/2003 | Frecker et al. |
| 2003/0069474 A1 | 4/2003 | Couvillon |
| 2003/0199870 A1 | 10/2003 | Truckai et al. |
| 2003/0207606 A1 | 11/2003 | Ho |
| 2003/0236531 A1 | 12/2003 | Couvillon |
| 2004/0002726 A1 | 1/2004 | Nunez et al. |
| 2004/0050971 A1 | 3/2004 | Rueger et al. |
| 2004/0054322 A1 | 3/2004 | Vargas |
| 2004/0068224 A1 | 4/2004 | Couvillon et al. |
| 2004/0097971 A1 | 5/2004 | Hughett |
| 2004/0138700 A1 | 7/2004 | Cooper et al. |
| 2004/0149802 A1 | 8/2004 | Whitman |
| 2004/0232195 A1 | 11/2004 | Shelton et al. |
| 2004/0232196 A1 | 11/2004 | Shelton et al. |
| 2004/0232197 A1 | 11/2004 | Shelton et al. |
| 2005/0006429 A1 | 1/2005 | Wales et al. |
| 2005/0006431 A1 | 1/2005 | Shelton et al. |
| 2005/0006434 A1 | 1/2005 | Wales et al. |
| 2005/0067457 A1 | 3/2005 | Shelton et al. |
| 2005/0067458 A1 | 3/2005 | Swayze et al. |

| | | | |
|---|---|---|---|
| 2005/0085693 | A1 | 4/2005 | Belson et al. |
| 2005/0102017 | A1 | 5/2005 | Mattison |
| 2005/0165415 | A1 | 7/2005 | Wales |
| 2005/0173490 | A1 | 8/2005 | Shelton |
| 2006/0016853 | A1 | 1/2006 | Racenet |
| 2006/0022014 | A1 | 2/2006 | Shelton et al. |
| 2006/0022015 | A1 | 2/2006 | Shelton et al. |
| 2006/0025810 | A1 | 2/2006 | Shelton |
| 2006/0025811 | A1 | 2/2006 | Shelton |
| 2006/0025812 | A1 | 2/2006 | Shelton |
| 2006/0025813 | A1 | 2/2006 | Shelton et al. |
| 2006/0025816 | A1 | 2/2006 | Shelton |
| 2006/0060630 | A1 | 3/2006 | Shelton et al. |
| 2006/0180634 | A1 | 8/2006 | Shelton et al. |
| 2006/0190028 | A1 | 8/2006 | Wales et al. |
| 2007/0084897 | A1 | 4/2007 | Shelton et al. |
| 2007/0102453 | A1 | 5/2007 | Morgan et al. |
| 2007/0170225 | A1 | 7/2007 | Shelton et al. |
| 2010/0181364 | A1 | 7/2010 | Shelton, Iv et al. |

FOREIGN PATENT DOCUMENTS

| | | |
|---|---|---|
| DE | 4303544 A1 | 9/1993 |
| DE | 19534320 C1 | 2/1997 |
| EP | 201883 A2 | 11/1986 |
| EP | 0500353 A1 | 8/1992 |
| EP | 0674876 | 4/1995 |
| EP | 0741966 A2 | 11/1996 |
| EP | 741996 A2 | 11/1996 |
| EP | 0 832 605 A | 4/1998 |
| EP | 0832605 A1 | 4/1998 |
| EP | 1323384 | 7/2003 |
| EP | 1 522 264 A | 4/2005 |
| EP | 1522264 A1 | 4/2005 |
| EP | 1621137 | 2/2006 |
| EP | 1621141 | 2/2006 |
| EP | 1621143 A2 | 2/2006 |
| EP | 1621151 A2 | 2/2006 |
| EP | 1693008 A1 | 8/2006 |
| NL | DE19537299 | 4/1997 |
| NL | DE19643073 | 4/1997 |
| NL | DE19647354 | 5/1998 |
| NL | DE1993372 | 2/2001 |
| WO | WO 99/02090 | 1/1999 |
| WO | WO-0078222 A1 | 12/2000 |
| WO | WO-0156455 | 8/2001 |
| WO | WO-0162158 A2 | 8/2001 |
| WO | WO-0162163 A1 | 8/2001 |
| WO | WO-0228268 | 4/2002 |
| WO | 03088845 A2 | 10/2003 |
| WO | 03090630 A2 | 11/2003 |
| WO | 03094746 A1 | 11/2003 |
| WO | WO 03/094743 | 11/2003 |
| WO | WO-03094743 A1 | 11/2003 |
| WO | WO-2004014238 A2 | 2/2004 |
| WO | WO 2004/050971 | 6/2004 |
| WO | WO-2004050971 A2 | 6/2004 |
| WO | 2004086987 A1 | 10/2004 |

OTHER PUBLICATIONS

Dec. 8, 2008, Office Action for U.S. Appl. No. 11/162,992.
U.S. Appl. No. 11/082,495, Mar. 17, 2005, Shelton, IV.
European Search Report for 05254681.9, dated May 15, 2009. (3 pages).
European Search Report for 05254700.7, dated May 15, 2009. (3 pages).
European Search Report for 05254699.1, dated May 15, 2009. (3 pages).
International Search Report for EP App. No. 06255053.8, Jan. 25, 2007.
International Search Report for EP App. No. 05254694.2, Jan. 12, 2006.
International Search Report for EP App. No. 05254685.0, Jan. 12, 2006.
International Search Report for EP App. No. 05254695.9, Jan. 12, 2006.
International Search Report for EP App. No. 05254680.1, Jan. 12, 2006.
Chinese Office Action for Application No. 200610146378.8 dated Jul. 24, 2009.
Chinese Office Action for Application No. 200610144755.4 dated Aug. 7, 2009.
Mar. 10, 2009, Office Action for Mexican Application No. PA/A/2005/008045.
Dec. 12, 2008 Office Action for U.S. Appl. No. 11/162,984.
Communication for 06 255 058.7, Jan. 11, 2007.
EPO Search Report dated Feb. 26, 2008 for Application No. 05254700.7.
EPO Search Report dated Feb. 29, 2008 for Application No. 05254681.9.
EPO Search Report dated Mar. 25, 2008 for Application No. 05254703.1.
EPO Search Report dated Mar. 3, 2008 for Application No. 05254699.1.
European Search Report for EP #05254684.3, dated Mar. 27, 2008.
European Search Report for EP 06255057.9, dated Oct. 19, 2007.
European Search Report for EPO Application No. 06255053, dated Jan. 25, 2007.
European Search Report for EPO Application No. 06255057, dated Jan. 29, 2007.
European Search Report for EPO Application No. 06255058, dated Jan. 31, 2007.
European Search Report for EPO Application No. 06255062, dated Nov. 23, 2006.
European Search Report for EPO Application No. 06255064, dated Feb. 9, 2007.
European Search Report for EPO Application No. 06255065, dated Feb. 15, 2007.
Guidelines for Hand and Power Tools' http://www.osha.gov/doc/outreachtraining/htmlfiles/tools.html. OSHA, May 1996, page 3.

* cited by examiner

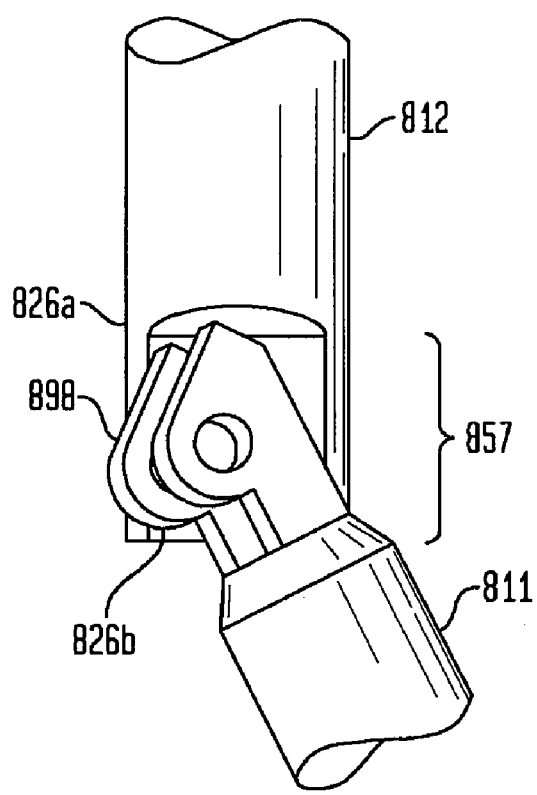

ELECTROACTIVE POLYMER-BASED ARTICULATION MECHANISM FOR MULTI-FIRE SURGICAL FASTENING INSTRUMENT

CROSS REFERENCE TO RELATED APPLICATIONS

This application is a continuation-in-part of U.S. patent application Ser. No. 11/082,495; now U.S. Pat. No. 7,506,790, filed on Mar. 17, 2005 and entitled "Surgical Instrument Incorporating an Electrically Actuated Articulation Mechanism," which claims priority to U.S. Provisional Application No. 60/591,694 filed on Jul. 28, 2004 and entitled "Surgical Instrument Incorporating an Electrically Actuated Articulation Mechanism." These applications are hereby incorporated by reference in their entireties.

FIELD OF THE INVENTION

The present invention relates broadly to surgical devices, and in particular to methods and devices for articulating and/or actuating an end effector on a surgical fastening instrument, such as a clip applier, hernia tacker, or skin stapler.

BACKGROUND OF THE INVENTION

Surgical fastening instruments carry a number of surgical fasteners which are typically placed to ligate a vessel, hemostatically staple and cut tissue, or to attach a prosthetic to tissue. All of these instruments contain a plurality of fasteners, which can be placed in a single firing, or in multiple firings. Single firing instruments, such as endocutters or various stapling instruments, contain a plurality of fasteners that are placed within tissue in a single firing. Multifire instruments, such as clip appliers and hernia tackers, contain a plurality of fasteners that are held within the surgical instrument, and the fasteners can be applied one at a time. These types of instruments can be fired repeatedly until the instrument runs out of fasteners or the surgery is complete.

One well known multifire instrument is a clip applier such as the ER320 LIGACLIP™ Multiple Clip Applier manufactured and sold by Ethicon EndoEND-Surgery, Cincinnati, Ohio. Clip appliers are used to close or ligate vessels during surgery, and are commonly used to ligate the cystic duct and cystic artery during the removal of a gall bladder. These surgical instruments can contain up to twenty clips and contain a feed shoe that pushes or feeds the clips distally within the instrument. In particular, a cam tube is advanced over jaws formed on the distal end of the device, thereby camming the jaws closed and crushing a clip disposed between. Some devices also simultaneously retract a feed bar while the cam tube is being advanced to reposition the feed bar in a position to advance the next clip. Once the clip is fully formed, the cam tube is retracted thereby releasing a return spring which is coupled to and advances the feed bar to advance the next clip into the jaws. Similar instruments can be used to deliver a hernia tack or skin staple.

One of the challenges with multifire devices is that a small stroke is repeatedly fired. The stroke must be controlled to allow for rapid repeat firing. Current mechanisms utilize mechanical linkages to accomplish this, however such linkages can be difficult to use in devices having a flexible shaft. In particular, the transfer of force from a handle to an end effector of a device having a flexible shaft can interfere with the tortuous orientation of the shaft, potentially causing it to straighten.

Accordingly, there remains a need for methods and devices for actuating surgical fastening instruments, such as clip appliers, hernia tackers, and skin staplers, and in particular for methods and devices that require a low force to effect actuation.

BRIEF SUMMARY OF THE INVENTION

The present invention provides various devices and methods for actuating and/or articulating a surgical fastening instruments, such as a clip applier, hernia tacker, or skin stapler. In one exemplary embodiment, a surgical fastener delivery device is provided having a housing with an elongate shaft extending therefrom, and a fastener advancing assembly extending through the housing and the elongate shaft, and movable to sequentially advance a plurality of clips through the elongate shaft. An electroactive polymer actuator is coupled to the fastener advancing assembly such that energy delivery to the electroactive polymer actuator will effect movement of the fastener advancing assembly to advance a plurality of clips through the elongate shaft.

In one embodiment, a surgical fastener delivery device is provided having an elongate shaft, and an end effector movably coupled to the elongate shaft by an articulation joint. The end effector can be configured to sequentially deliver a plurality of fasteners to tissue. The device can also include an electroactive polymer actuator coupled to the articulation joint and adapted to move the end effector about the articulation joint relative to the elongate shaft when energy is delivered to the electroactive polymer actuator.

While various techniques can be used to move the articulation joint using the end effector, in one embodiment the elongate shaft can include a slide bar extending therethrough and having a distal end coupled to the articulation joint. The electroactive polymer actuator can be configured to move the slide bar laterally to effect movement of the end effector. For example, the electroactive polymer actuator can include first and second electroactive polymer actuators disposed on opposed sides of the slide bar. The slide bar can include gears formed on a distal end thereof and adapted to engage corresponding gears formed in the articulation joint. In another embodiment, the articulation joint can be in the form of a pivot joint, and the electroactive polymer actuator can include a first electroactive polymer actuator extending between a first side of the end effector and a first side of the elongate shaft, and a second electroactive polymer actuator extending between a second opposed side of the end effector and a second opposed side of the elongate shaft. In yet another embodiment, the articulation joint can be in the form of a flexible portion formed between the elongate shaft and the end effector. The electroactive polymer actuator can include a plurality of electroactive polymer actuators coupled to the flexible portion at distinct locations, each of the plurality of electroactive polymer actuators being configured to change orientations when energy is selectively delivered thereto to flex the flexible portion.

A method for fastening tissue is also provided and in one embodiment includes inserting an elongate shaft of a fastener delivery device into a body lumen to position an end effector movably coupled to a distal end of the elongate shaft adjacent to a surgical site, delivering energy to an electroactive polymer actuator to angularly position the end effector relative to the elongate shaft, and sequentially actuating the device to sequentially deliver a plurality of fasteners to tissue disposed adjacent to the end effector. Delivering energy to the electroactive polymer actuator can cause the electroactive polymer actuator to radially expand to move a slide bar, extending through the elongate shaft and coupled to an articulation joint formed between the elongate shaft and the end effector, laterally and thereby effect pivotal movement of the end effector. Alternatively, delivering energy to the electroactive polymer actuator can cause the electroactive polymer actuator to axially contract move a slide bar, extending through the elongate shaft and coupled to an articulation joint formed between the elongate shaft and the end effector, laterally and thereby effect pivotal movement of the end effector. In other embodiments, energy can be delivered to a first electroactive polymer actuator to move the end effector in a first direction, and to a second electroactive polymer actuator to move the end effector in a second, opposed direction. The amount of energy delivered to the electroactive polymer actuator can correspond to a degree of movement of the end effector. In yet another embodiment, delivering energy to an electroactive polymer actuator can angularly position the end effector relative to the elongate shaft by flexing a flexible portion extending between the elongate shaft and the end effector.

In another embodiment, an electroactive polymer actuator can be effective to actuate a fastener advancing assembly. While the electroactive polymer actuator can effect movement of the fastener advancing assembly using a variety of techniques, in one embodiment the electroactive polymer actuator can be disposed within the housing. For example, the electroactive polymer actuator can be coupled to a proximal portion of the fastener advancing assembly. Energy delivery to the electroactive polymer actuator can cause the electroactive polymer actuator to apply a force to the fastener advancing assembly to move the fastener advancing assembly distally to advance a plurality of fasteners through the elongate shaft. In particular, energy delivery to the electroactive polymer actuator can cause the electroactive polymer actuator to axially expand to move the fastener advancing assembly from a proximal position to a distal position. The housing can optionally include an actuation mechanism, such as a trigger, formed thereon and adapted to actuate electrical energy delivery to the electroactive polymer actuator. The trigger can also be adapted to advance the fastener advancing assembly in conjunction with the electroactive polymer actuator.

In another embodiment, the electroactive polymer actuator can be disposed within the elongate shaft. For example, the electroactive polymer actuator can be adapted to apply a force to a distal-most portion of the fastener advancing assembly when energy is delivered to the electroactive polymer actuator to advance the distal-most portion of the fastener assembly toward a distal end of the elongate shaft. In an exemplary embodiment, where the fastener deliver device includes an articulation joint formed on the elongate shaft and configured to allow a distal end portion of the elongate shaft to be angularly positioned relative to a proximal portion of the elongate shaft, the electroactive polymer actuator can be coupled to the fastener advancing assembly at a location distal to the articulation joint.

Exemplary methods for delivering a fastener to tissue are also provided, and in one embodiment the method can include positioning a distal end of an elongate shaft of a fastener delivery device adjacent to tissue to be fastened, and delivering energy to an electroactive polymer actuator disposed within the fastener delivery device to advance a fastener through the elongate shaft and to thereby fasten the tissue. Energy delivery to the electroactive polymer actuator can cause the electroactive polymer actuator to expand to move a fastener advancing assembly through the elongate shaft, thereby causing the fastener advancing assembly to sequentially advance a plurality of fasteners. In one embodiment, the electroactive polymer can apply a force to a proximal portion of the fastener advancing assembly that is disposed within a housing of the fastener delivery device. In another embodiment, the electroactive polymer can cause the electroactive polymer actuator to apply a force to a distal portion of the fastener advancing assembly that is disposed within the elongate shaft of the fastener delivery device. Energy can be delivered to the electroactive polymer actuator using a variety of techniques, but in one embodiment energy can be delivered to the electroactive polymer by actuating a trigger movably coupled to a handle housing of the fastener advancing assembly. The trigger can also advance the fastener advancing assembly in conjunction with the electroactive polymer actuator.

BRIEF DESCRIPTION OF THE DRAWINGS

The invention will be more fully understood from the following detailed description taken in conjunction with the accompanying drawings, in which:

FIG. 8 is a partially cross-sectional view of another embodiment of an end effector movably coupled to a distal portion of an elongate shaft of a fastener delivery device, showing EAP actuators for articulating the end effector;

DETAILED DESCRIPTION OF THE INVENTION

Figure 1A:
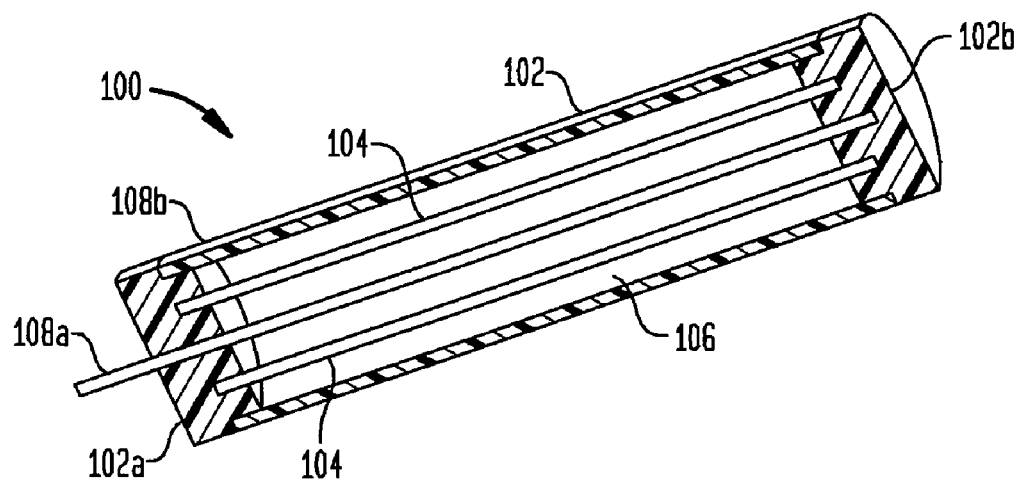
FIG. 1A is a cross-sectional view of a prior art fiber bundle type EAP actuator.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for effecting movement of one or more components of a multifire device, such as a clip applier, hernia tacker, or skin stapler. In one exemplary embodiment, a surgical fastening instrument is provided having an elongate shaft with an end effector coupled thereto and adapted to apply one or more surgical fasteners to tissue. An electrically expandable and contractible actuator, such as an electroactive polymer actuator, can be used to drive a fastener advancing or forming assembly through the elongate shaft, thereby driving a surgical fastener into tissue. A person skilled in the art will appreciate that the surgical fastening instrument can have a variety of configurations, and that one or more electroactive polymer actuators can be coupled to one or more components of the surgical fastening instrument to effect movement.

Electroactive Polymers

Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1 V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect that is caused when voltage is applied.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long stands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. The fibers can alternatively be configured to expand or lengthen. An example of a commercially available fiber EAP material is manufactured by Santa Fe Science and Technology and sold as PANION™ fiber and described in U.S. Pat. No. 6,667,825, which is hereby incorporated by reference in its entirety.

Figure 1B:
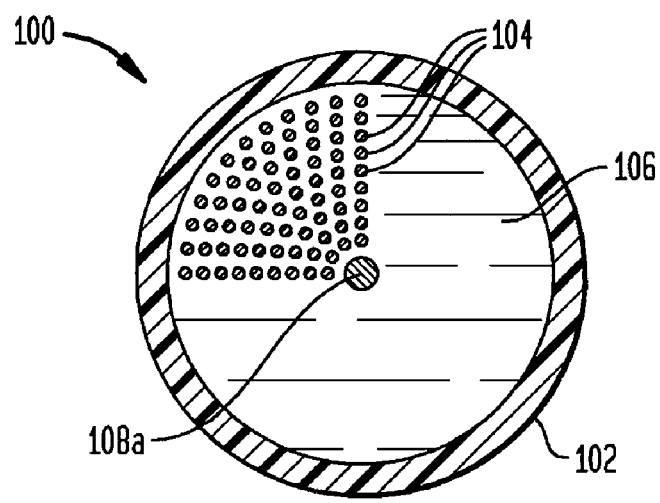
FIG. 1B is a radial cross-sectional view of the prior art actuator shown in FIG. 1A.

FIGS. 1A and 1B illustrate one exemplary embodiment of an EAP actuator 100 formed from a fiber bundle. As shown, the actuator 100 generally includes a flexible conductive outer sheath 102 that is in the form of an elongate cylindrical member having opposed end caps 102a, 102b formed thereon. The outer sheath 102 can, however, have a variety of other shapes and sizes depending on the intended use. As is further shown, the outer sheath 102 is coupled to an energy delivering electrode 108a and a return electrode 108b. In the illustrated embodiment, the energy delivering electrode 108a extends through one of the end caps, e.g., end cap 102a, through the inner lumen of the conductive outer sheath 102, and into the opposed end cap, e.g., end cap 102b. The energy delivering electrode 108a can be, for example, a platinum cathode wire, and it can be coupled to any portion of the outer sheath 102. The conductive outer sheath 102 can also include an ionic fluid or gel 106 disposed therein for transferring energy from the energy delivering electrode 108a to the EAP fibers 104, which are disposed within the outer sheath 102. In particular, several EAP fibers 104 are arranged in parallel and extend between and into each end cap 102a, 102b. As noted above, the fibers 104 can be arranged in various orientations to provide a desired outcome, e.g., radial expansion or contraction, or bending movement. In use, energy can be delivered to the actuator 100 through the active energy delivering electrode 106a. The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 102b will be pulled toward one another, thereby contracting and decreasing the length of the flexible outer sheath 102.

The other type of EAP is a laminate structure, which consists of one or more layers of an EAP, a layer of ionic gel or fluid disposed between each layer of EAP, and one or more flexible plates attached to the structure. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 2A:
FIG. 2A is a cross-sectional view of a prior art laminate type EAP actuator having multiple EAP composite layers.
Figure 2B:
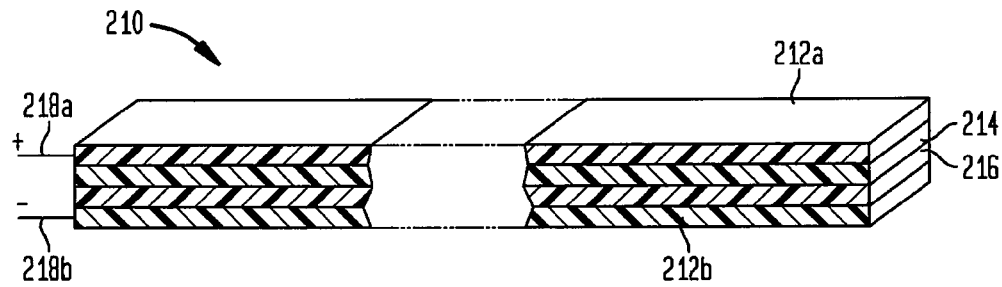
FIG. 2B is a perspective view of one of the composite layers of the prior art actuator shown in FIG. 2A.

FIGS. 2A and 2B illustrate an exemplary configuration of an EAP actuator 200 formed from a laminate. Referring first to FIG. 2A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 2B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 2B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

EAP Actuation

As previously indicated, in an exemplary embodiment methods and devices are provided that utilize electrically expandable and contractible actuators, such as EAP actuators, to effect actuation of various components of a surgical fastening instrument. In an exemplary embodiment, the surgical fastening instrument is a multifire instrument that is configured to sequentially deliver multiple fasteners to a target site. Exemplary multifire instruments include, by way of non-limiting example, clip appliers, hernia tackers, and skin staplers. A person skilled in the art will appreciate that these instruments can have virtually any configuration, and that the instruments illustrated and described herein are merely relied on to demonstrate use of an electroactive polymer actuator to effect actuation. The actuation mechanisms using electroactive polymer actuators can be incorporated into virtually any surgical fastener delivery device known in the art. The EAP actuators can also have a variety of configurations, and the actuators can be in the form of the laminate type EAP or the fiber-bundle type EAP. In an exemplary embodiment, the EAP actuator(s) is in the form of a laminate or composite EAP that is configured to expand in a direction of desired movement, e.g., along a longitudinal axis of the device.

Figure 3A:
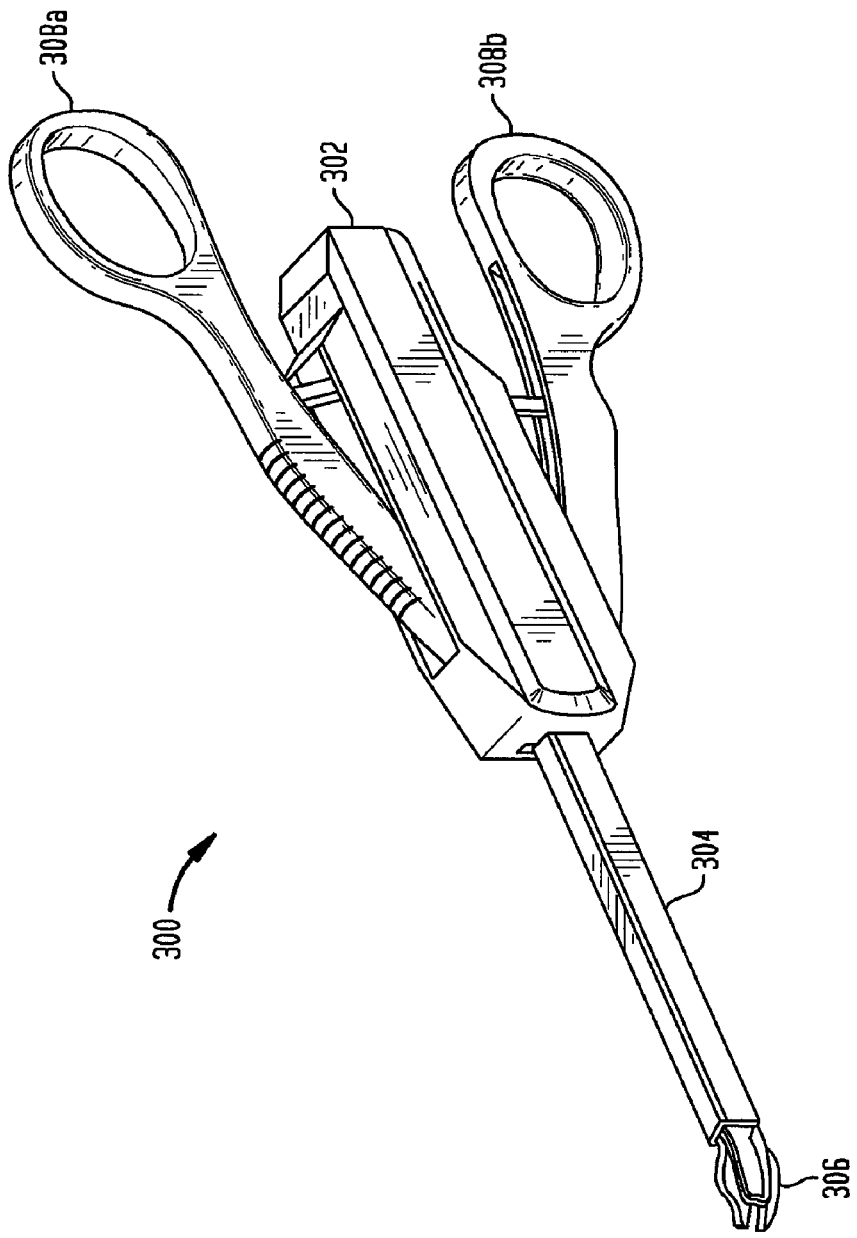
FIG. 3A is perspective view of one embodiment of a surgical clip applier.

FIG. 3A illustrates one exemplary embodiment of a surgical fastener device in the form of a clip applier 300. As shown, the clip applier 300 generally includes a handle housing 302 having an elongate shaft 304 extending distally therefrom. A pair of opposed jaws 306 are formed on a distal end of the elongate shaft 304, and they are adapted to receive a clip therebetween and to deform the clip to engage tissue. The illustrated device 300 also includes first and second triggers 308a, 308b coupled thereto and movable from an open position to a closed position to advance multiple clips though the elongate shaft to position a clip within the jaws, and to close the jaws 306 to deform the clip around tissue disposed between the opposed jaws 306. While two triggers 308a, 308b are shown, a person skilled in the art will appreciate that the device 300 can include any number of triggers, or alternatively or additionally it can include other actuating mechanisms, such as a knob, dial, lever, etc.

Figure 3B:
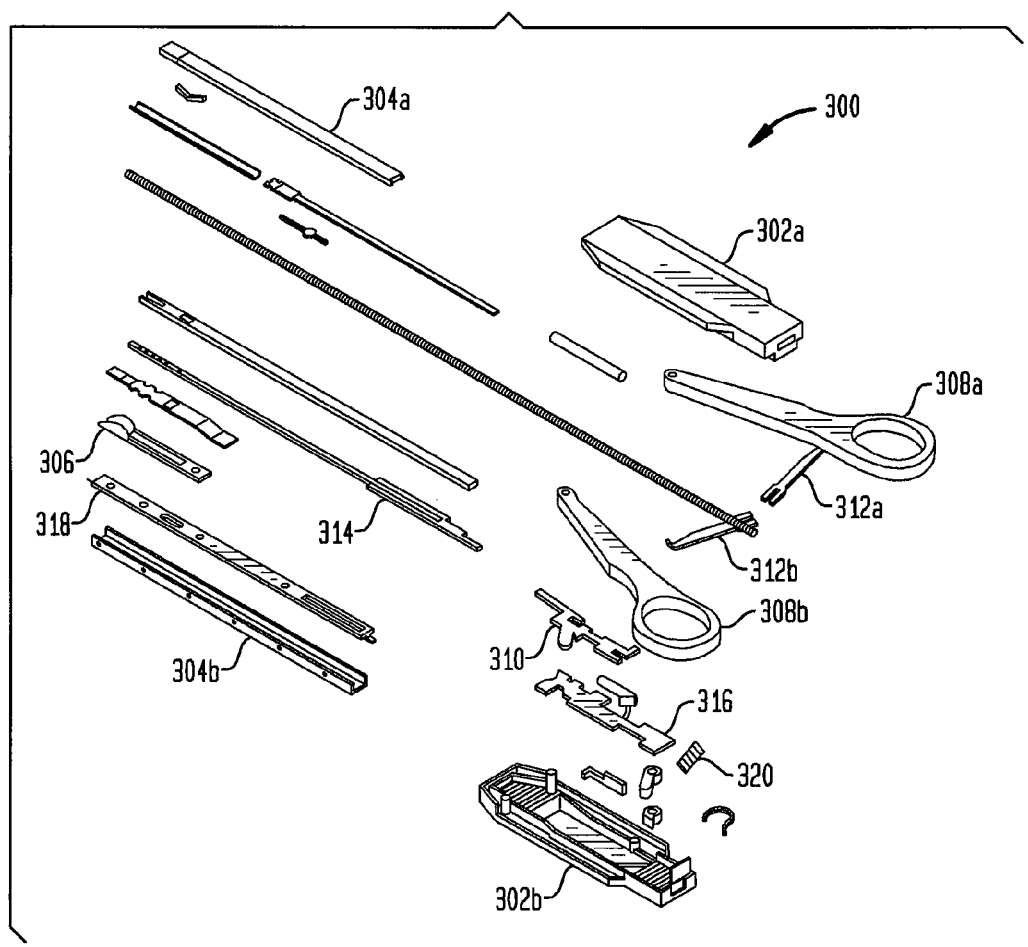
FIG. 3B is an exploded view of the surgical clip applier shown in FIG. 3A.

FIG. 3B illustrates the internal components of the clip applier 300 shown in FIG. 3A. In general, the clip applier 300 includes a clip advancing assembly for advancing a clip through the elongate shaft 304, and a clip closing assembly for closing the jaws 306 to deform a clip disposed therebetween. While the clip advancing assembly and the clip closing assembly can each have a variety of configurations, in the embodiment shown in FIG. 3B each assembly includes several components which are linked together and which are movable between a proximal position and a distal position when the triggers 308a, 308b are closed. In particular, the clip advancing assembly includes a clip feed plate 310 disposed within the handle housing (two housing halves 302a, 302b are shown) and coupled at its proximal end to the triggers 308a, 308b by a pair of proximal lever arms 312a, 312b. The lever arms 312a, 312b are effective to move the clip feed plate 310 and the other components of the clip advancing assembly in a proximal direction when the triggers 308a, 308b are closed. A distal end of the clip feed plate 310 is coupled to a feed bar 314 having a distal end that is adapted to advance a clip into the jaws 306. The clip closing assembly includes a clip closing plate 316 that is disposed within the housing and that is coupled at a distal end to a cam channel 318 that is adapted to close the jaws 306. The clip closing assembly also includes an electrically expandable and contractible actuator, such as an EAP actuator 320, as will be discussed in more detail below, that is configured to apply a force to the clip closing plate 316 to drive the clip closing plate 316 and cam channel 318 distally, thereby closing the jaws 306 to deform a clip disposed therebetween. The device 300 can also include other elements to facilitate clip advancing and clip closing. By way of non-limiting example, other exemplary components are disclosed in U.S. Pat. No. 5,431,668 filed on Apr. 29, 1993 and entitled "Clip Applier," and in U.S. Pat. No. 5,171,249 filed on Apr. 4, 1991 and entitled "Endoscopic Multiple Ligating Clip." These patents are commonly assigned to Ethicon, Inc., and are hereby incorporated by reference in their entireties.

Figure 3C:
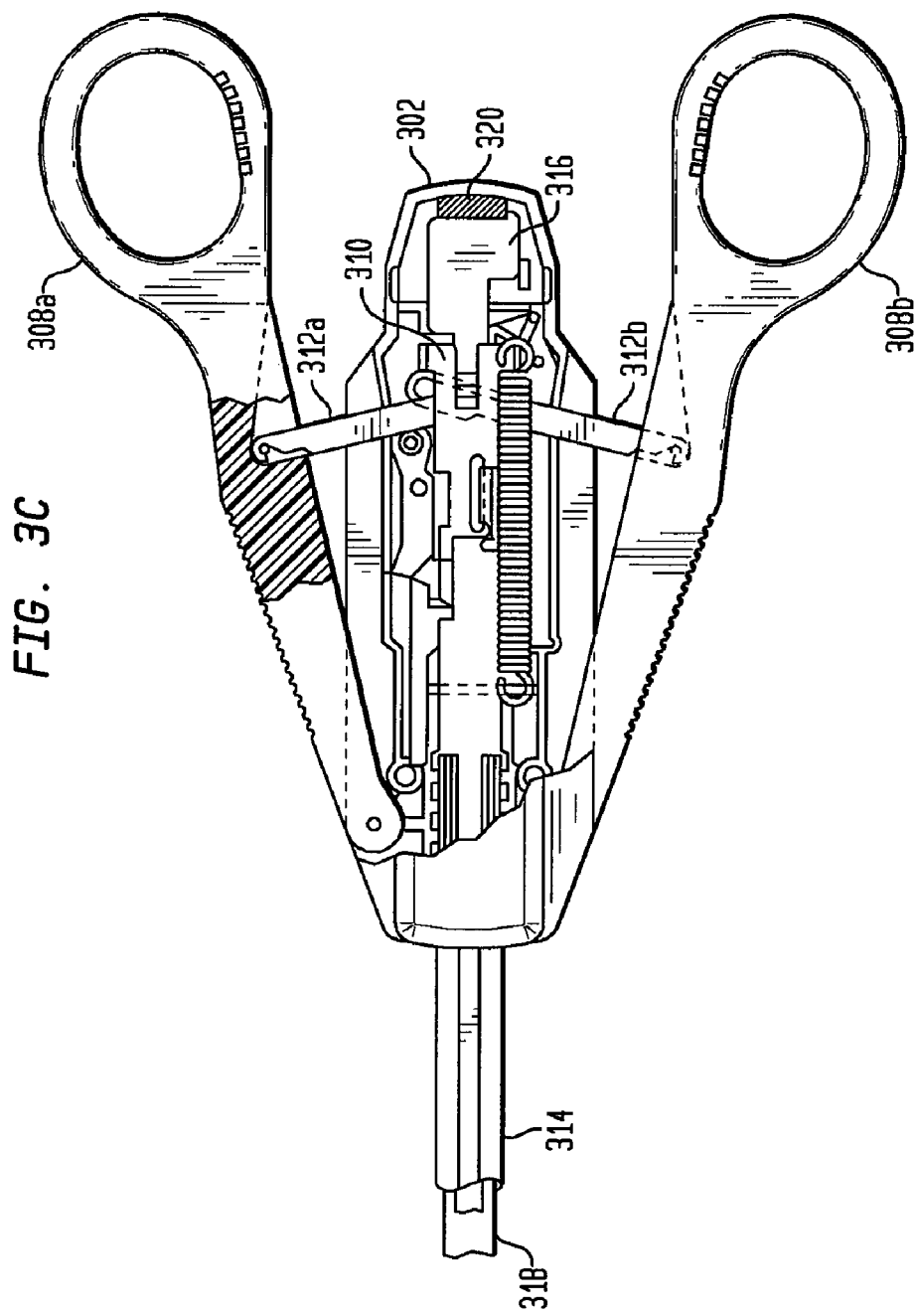
FIG. 3C is a cross-sectional view of the handle housing of the surgical clip applier shown in FIGS. 3A and 3B.

The EAP actuator is shown in more detail in FIG. 3C, and as shown, the EAP actuator 320 is positioned between a proximal-most end of the clip closing plate 310 and the inner proximal-most wall of the housing 302. While not shown, the EAP actuator 320 can include electrodes extending therefrom and coupled to a power source, such as a battery, disposed within the housing 302, or the electrodes can be configured to couple to an external power source, such as a electrical outlet via an electrical cord. Energy delivery to the EAP actuator 320 can be actuated using a mechanism, such as a trigger, button, lever, sliding knob, rotating dial, etc., formed on the handle housing 302. For example, the triggers 308a, 308b can be configured to initiate energy delivery by establishing an electrical connection point between a portion of each trigger 308a, 308b and the EAP actuator 320. A person skilled in the art will appreciate that a variety of techniques known in the art can be used to initiate energy delivery to the EAP actuator 320.

When energy is delivered to the EAP actuator 320, the actuator 320 will expand in a distal direction (contracting in an opposite direction). As a result, the EAP actuator 320 will apply a distally-directed force to the clip closing plate 310, advancing the clip closing plate 310 distally and thus advancing the cam channel 318, which is coupled to the clip closing plate 310, distally to cause the cam channel 318 to close the jaws 306 and deform a clip disposed therebetween. When energy delivery is terminated, the EAP actuator 320 can return to its initial configuration, as shown in FIG. 3C, allowing the clip closing plate 310 and cam channel 318 to return to their proximal position. In order to facilitate proximal movement of the clip closing plate 310 when energy delivery to the EAP actuator 320 is terminated, a biasing element, such as a spring, can be coupled to the clip closing plate 310 to bias the plate 310 to the proximal position.

While not shown, additionally or alternatively an EAP actuator can be used to move the clip advancing assembly to advance a clip into the jaws 306. For example, an EAP actuator can be disposed within the handle housing 302 at a location in which it is effective to apply a distally-directed force to the clip feed plate 310, thereby advancing the clip feed plate 310 and clip feed bar 314 distally to advance a clip into the jaws. The timing of electrical energy delivery to an EAP actuator coupled to the clip advancing and clip closing assemblies can also vary. For example, movement of the triggers 308a, 308b, or some other actuation mechanism, can be effective to first deliver energy to an EAP actuator coupled to the clip advancing assembly to advance a clip into the jaws. Energy delivery to the clip advancing assembly can then be terminated, and energy can be delivered to an EAP actuator coupled to the clip closing assembly to close the jaws to deform the clip. Alternatively, energy delivery can occur simultaneously. In other embodiments, an EAP actuator can be configured to apply a proximally-directed force to the clip advancing and/or clip closing assembly. For example, the clip advancing assembly can be biased to a distal position, and energy can be delivered to an EAP actuator to move the clip advancing assembly to a proximal position, in which the clip advancing assembly is positioned behind the next clip to be advanced. Once energy delivery is terminated, the clip advancing assembly can return to its distal position, thereby advancing a clip into the jaws. A person skilled in the art will appreciate that EAP actuator(s) can be used to effect movement of various components of a surgical fastening instrument.

While FIG. 3C illustrates one embodiment of an EAP actuator disposed within a handle housing for driving a proximal portion of a clip advancing and/or clip closing assembly of a surgical fastener delivery device, in other embodiments one or more EAP actuators can be disposed within the elongate shaft of a surgical fastening device. Such a configuration is particularly advantageous as it allows the elongate shaft to be flexible or to have an articulation joint formed thereon. The EAP actuator could be disposed distal of the flexible portion or articulation joint such that it will not interfere with pivotal movement of the end effector relative to the elongate shaft.

Figure 4A:
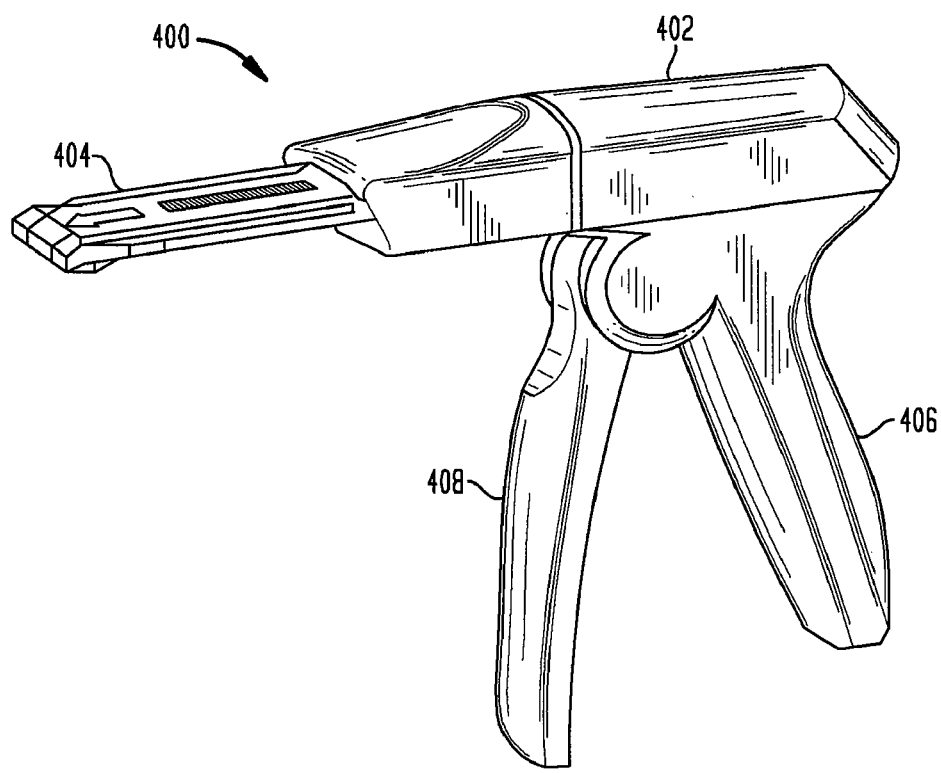
FIG. 4A is a perspective view of one embodiment of a skin stapler.
Figure 4B:
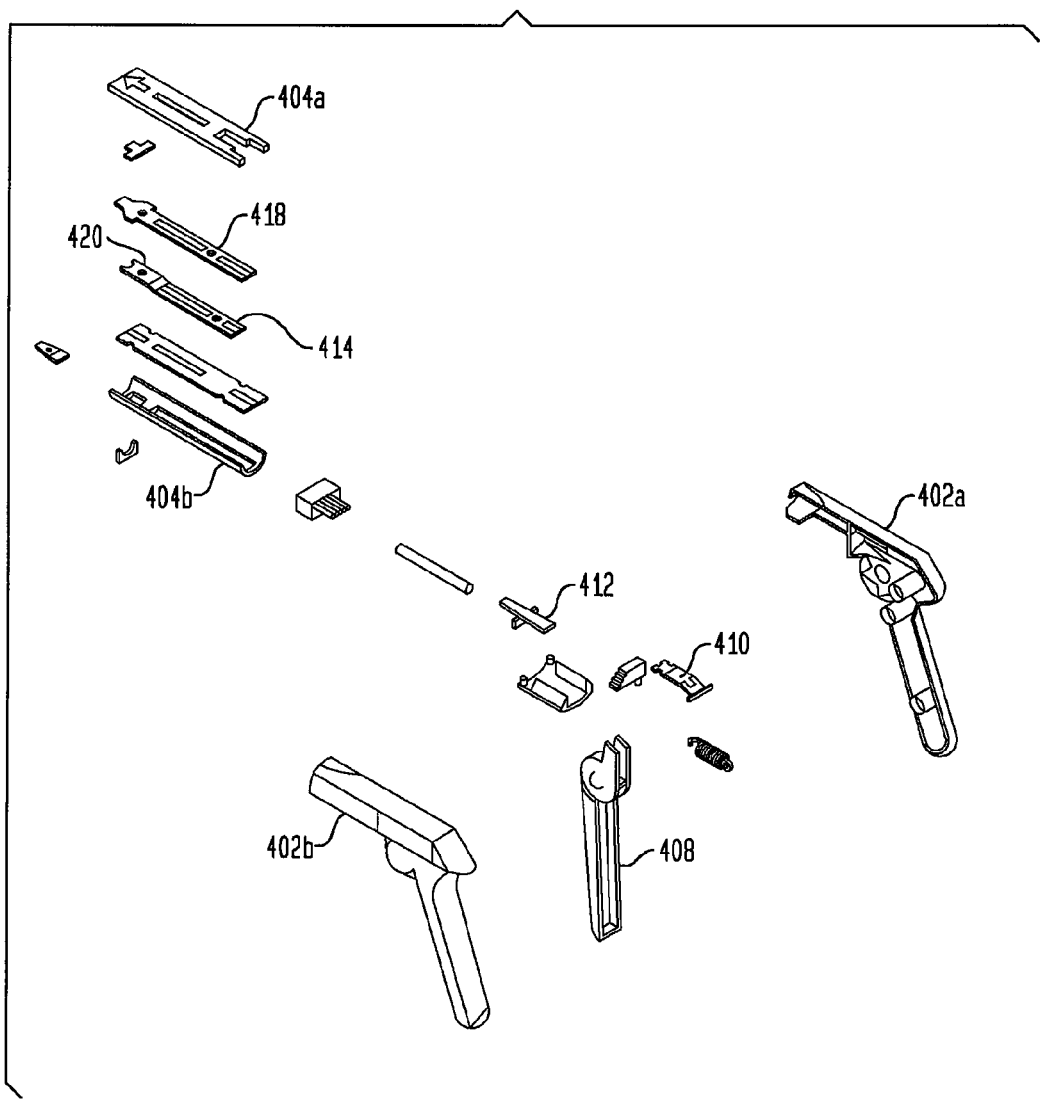
FIG. 4B is an exploded view of the skin stapler shown in FIG. 4A.

By way of non-limiting example, FIGS. 4A-4B illustrates one embodiment of a skin stapler 400 having an EAP actuator 420 disposed within the elongate shaft for advancing a staple. In general, as shown in FIG. 4A, the skin stapler 400 includes a handle housing 402 having an elongate shaft 404 extending distally therefrom. The handle housing 402 includes a stationary trigger 406, and a trigger 408 that is movably coupled to the handle housing 402. As previously explained with respect to the clip applier 300 of FIG. 3A, the skin stapler 400 can include any number of triggers and/or other actuating mechanisms, such as a knob, button, dial, or lever.

The internal components of the skin stapler 400 are shown in more detail in FIG. 4B, and as shown the device 400 generally includes a single staple advancing/forming assembly that is adapted to advance a series of staples through the elongate shaft 404, and to deform a distal-most staple around an anvil to staple tissue positioned adjacent to the distal end of the elongate shaft. In particular, the staple advancing/forming assembly includes a drive block 410 that is disposed within the handle housing (two housing halves 402a, 402b are shown), a drive train 412 coupled to a distal end of the drive block 410, and a staple former 414 coupled to a distal end of the driver train 412 and extending through the elongate shaft (two shaft housing halves 404a, 404b are shown). An EAP actuator 420, which will be discussed in more detail below, is formed on a portion of the staple former 414 and it is configured to apply a force to the staple former 414 to advance the at least a portion of the staple former 414 distally toward an anvil 418, thereby deforming a staple around the anvil 418. The skin stapler 400 can also include other elements to facilitate staple advancing and forming. By way of non-limiting example, other exemplary components are disclosed in U.S. Pat. No. 5,330,087 filed on May 14, 1993 and entitled "Rotating Head Skin Stapler," which is assigned to Ethicon, Inc., and which is hereby incorporated by reference in its entirety.

Figure 4C:
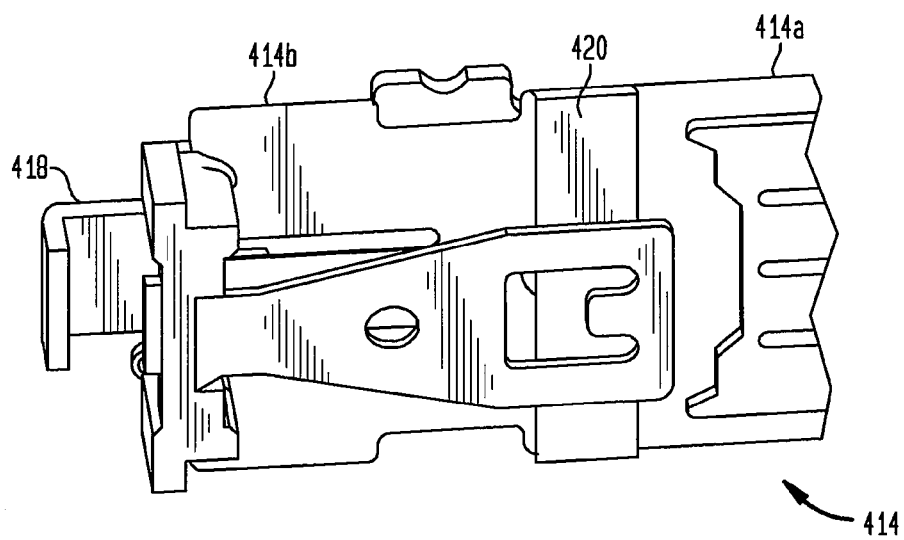
FIG. 4C is a perspective view of a distal portion of a fastener advancing assembly of the skin stapler shown in FIGS. 4A and 4B.

The EAP actuator 420 is shown in more detail in FIG. 4C, and as shown the EAP actuator 420 forms a linkage between a proximal portion 414a of the staple former 414 and a distal portion 414b of the staple former 414. In particular, the staple former 414, which extends through the elongate shaft 404, is formed from two separate pieces, i.e., proximal and distal portions 414a, 414b. The EAP actuator 420 is coupled to and extends between the proximal and distal portions 414a, 414b to link the portions 414a, 414b to one another. As a result, when energy is delivered to the EAP actuator 420, the EAP actuator 420 will expand in a direction that moves the distal portion 414b of the staple former 414 in a distal direction relative to the proximal portion 414a of the staple former 414. The distal portion 414b will thus advance a staple to deform the staple against the anvil 418, thereby stapling tissue positioned adjacent to the distal end of the elongate shaft 402. A person skilled in the art will appreciate that the EAP actuator can alternatively be disposed between a fixed member, such as a portion of the elongate shaft 402, and the staple former 414, rather than between proximal and distal portions 414a, 414b of the staple former 414. The EAP actuator can also have a variety of other configurations which allow it to effect distal movement of the staple former 414. While not shown, the device 400 can also include an articulation joint, exemplary embodiments of which will be discussed in more detail below. Where an articulation joint is provided to allow the end effector or distal portion of the shaft 404 to be angularly oriented relative to the shaft 404, the EAP actuator is preferably disposed distal of the articulation joint such that actuation does not interfere with articulation of the end effector.

Figure 5:
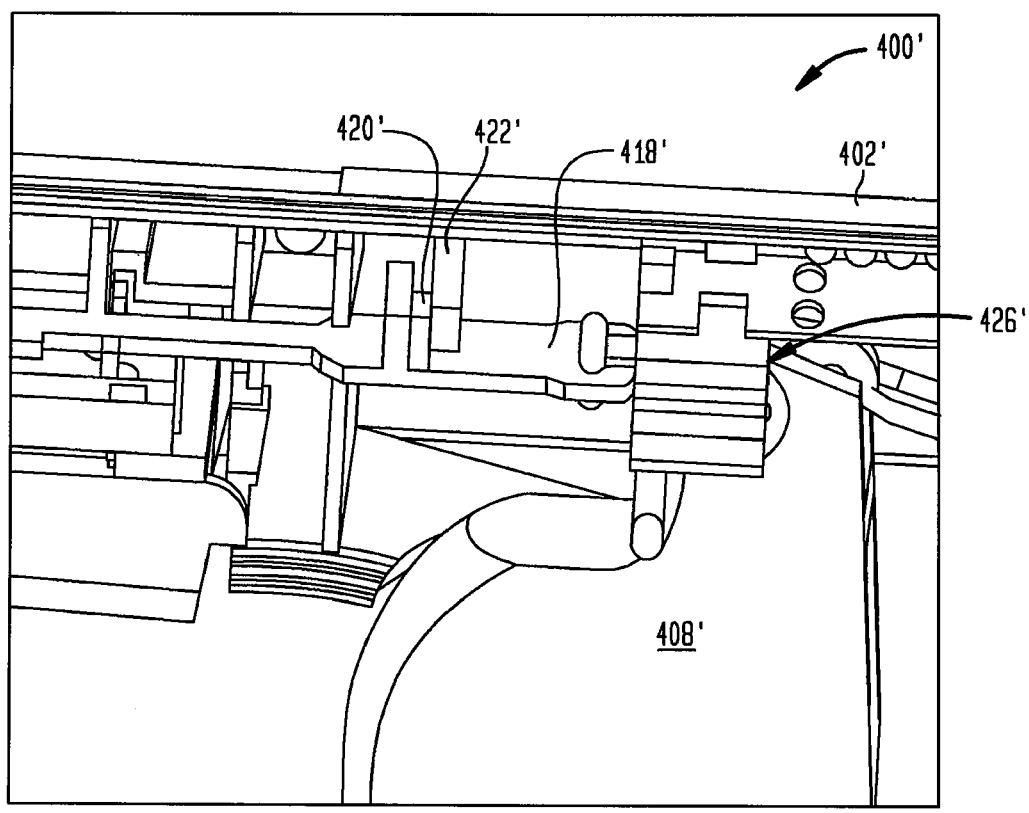
FIG. 5 is a perspective view of a portion of a handle housing of a skin stapler in accordance with another embodiment.

While FIGS. 3C and 4C illustrate embodiments of EAP actuators that replace mechanical actuators for driving a fastener forming and/or advancing assembly, in other embodiments one or more EAP actuators can be used in conjunction with a mechanical actuator to reduce the amount of force required to effect actuation, i.e., the EAP actuator(s) can assist the mechanical drive mechanism. By way of non-limiting example, FIG. 5 illustrates a handle housing 402' of a skin stapler 400' that is similar to the skin stapler 400 shown in FIGS. 4A-4B, but that includes an EAP actuator that works in conjunction with the trigger to deliver a fastener. In particular, an EAP actuator 420' is disposed between a fixed wall or protrusion 422' extending from the housing (only one housing half 402' is shown), and a wall or protrusion 422' formed on the drive block 418'. Energy delivery to the EAP actuator 420' causes the EAP actuator 420' to expand, thereby advancing the drive block 418', as well as the drive train and staple former (not shown), distally to advance a staple and deform the staple around the anvil. As is further shown in FIG. 5, the movable trigger 408' is configured to engage and drive the drive block 418' distally when the trigger 408' is pivoted to the closed position. Thus, when energy is delivered to the EAP actuator 420', the EAP actuator 420' will assist the trigger 408' to drive the drive block 418', drive train, and staple former distally to deform a staple around the anvil.

In an exemplary embodiment, an electrical connection can be established at a point of contact 426' between the trigger 408' and the drive block 418', such that energy delivery to the EAP actuator 420' will be activated when the trigger 408' comes into contact with the drive block 418'. As a result, energy is only delivered to the EAP actuator 420' when the trigger 408' is being closed to drive the drive block 418', drive train, and staple former distally to deform a staple around the jaws. When the trigger 408' is released to return to its open position, energy delivery to the EAP actuator 420' is terminated such that the EAP actuator 420' will contract to allow the drive block 418' to return to its proximal position. A person skilled in the art will appreciate that the EAP actuator can be positioned at various other locations, and that the trigger can alternatively be in the form of a button, lever, knob, dial, etc.

In use, each of the aforementioned devices can be delivered through a lumen, e.g., via a cannula or trocar, to position a distal end of the device adjacent to tissue. A trigger and/or other actuator disposed on the handle housing can then be actuated to deliver energy to the EAP actuator(s). Energy can be supplied from an internal energy source, such as a battery, or from an external energy source, such as an external battery or via an electrical outlet. The energy can be delivered to the EAP actuator(s) via an electrode, as previously described, which can extend through the handle housing and optionally through the elongate shaft, depending on the location of the EAP actuator. Once energy is delivered to the EAP actuator, the EAP actuator will expand in a direction (and contract in a transverse direction) that will apply a force to the fastener advancing and/or forming assembly to move the assembly relative to the elongate shaft. In an exemplary embodiment, the EAP actuator drives the fastener closing assembly distally, thereby driving one or more fasteners through the shaft, and causing a distal-most fastener to advance into tissue (e.g., staple tissue), or to deform around tissue to engage the tissue (e.g., clip tissue). Where the device includes a separate fastener advancing assembly, the EAP actuator, or a separate EAP actuator, can be used to drive the fastener advancing assembly in a distal direction with the fastener closing assembly, or alternatively in a proximal direction to position the fastener advancing assembly proximal to the next clip to be advanced, as previously explained. Termination of energy delivery to the EAP actuator will cause the EAP actuator to return to its resting configuration, thereby moving the fastener advancing and/or forming assembly in an opposite direction. One or more biasing elements, such as springs, can also be used to facilitate movement of the fastener advancing and/or forming assembly to their initial resting position.

Articulation

As previously indicated, the present invention also provides exemplary methods and devices for articulating a surgical fastening instrument. FIGS. 6A-12B illustrate various exemplary embodiments of articulation joints and electroactive polymer actuators for effecting articulation. These articulation joints can be incorporated into any surgical fastening instrument, including those exemplary prior art instruments described above.

Figure 6A:
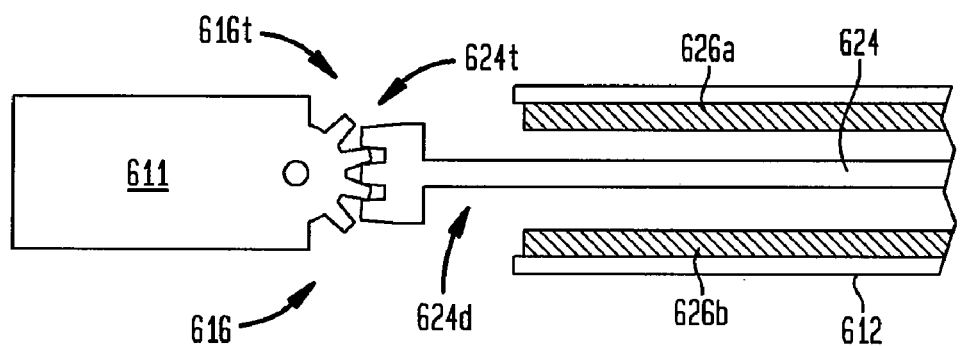
FIG. 6A is a cross-sectional view of a distal portion of a fastener delivery device, showing EAP actuators in a non-actuated configuration for effecting articulation of an end effector of the fastener delivery device.
Figure 6B:
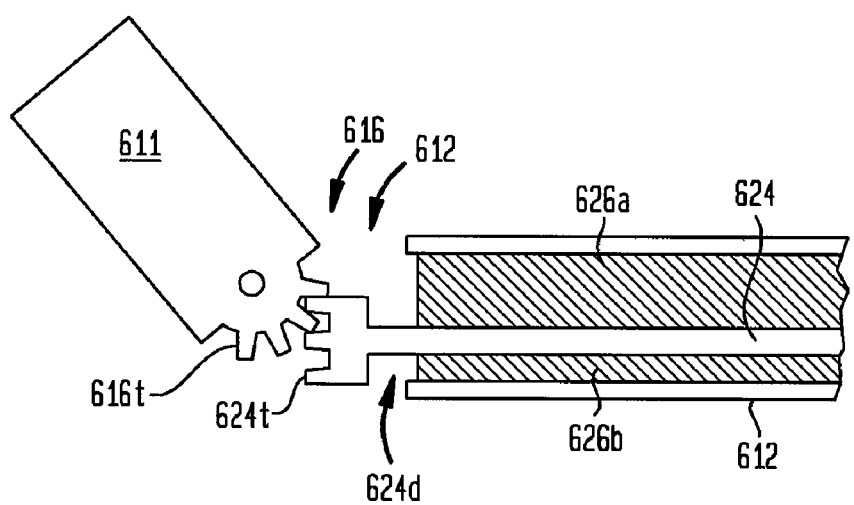
FIG. 6B is a cross-sectional view of the distal portion of the fastener delivery device shown in FIG. 6A, showing one of the EAP actuators electrically actuated to articulate the end effector.

Referring first to FIGS. 6A-6B, a distal end 612b of the elongate shaft 612 is shown coupled to a proximal end of the end effector 611 by a pivot joint 616, such that the end effector 611 can pivot relative to the shaft 612 about the pivot joint 616. The device also includes a slide bar 624 extending through the elongate shaft 612 and having a distal end 624d with gear teeth 624t formed thereon and adapted to engage corresponding gear teeth 616t formed on the end effector 611. The device can also include one or more electrically expandable and contractible actuators, such as an EAP actuator, for moving the slide bar 624 to cause the gear teeth 624t on the slide bar 624 to move the gear teeth 624t on the end effector 611 and thereby pivot the end effector 611 relative to the elongate shaft 612. While the EAP actuator(s) can effect movement of the slide bar 624 using a variety of techniques, in one exemplary embodiment the EAP actuators are configured to move the slide bar 624 laterally. In particular, a first EAP actuator 626a can extend through at least a portion of the elongate shaft 612 adjacent to a first lateral side of the slide bar 624, and a second EAP actuator 626b can extend through at least a portion of the elongate shaft 612 adjacent to a second, opposed lateral side of the slide bar 624, as shown in FIGS. 6A-6B. Either type of EAP actuator can be used, but in an exemplary embodiment the EAP actuators 626a, 626b are laminate type EAP actuators that are adapted to expand laterally when energy is delivered thereto. FIG. 6A illustrates both actuators 626a, 626b in a non-expanded, un-actuated configuration, where no energy is delivered to either actuator 626a, 626b. FIG. 6B illustrates the first EAP actuator 626a laterally expanded to move the slide bar 624 laterally toward the second EAP actuator 626b, thereby causing the slide bar 624 to pivot the end effector 611 in a direction opposite to the direction of movement of the slide bar 624. Energy can be delivered to the actuators 626a, 626b through electrodes extending through the shaft 612 and coupled to an energy source disposed within or coupled to a handle of the device, e.g., a battery source or an electrical outlet or other energy source. The handle can also include a control mechanism, such as a sliding lever, rotatable knob, or dial, coupled thereto and adapted to control the amount of energy delivered to each actuator 626a, 626b. The amount of energy delivered to each actuator 626a, 626b is determinative of the amount of expansion of the actuators 626a, 626b, thus allowing the amount of pivotal movement of the end effector 611 to be selectively adjusted.

A person skilled in the art will appreciate that, while FIGS. 6A-6B illustrate a laterally-moving slide bar 624 with laterally expanding EAP actuators 626a, 626b, the slide bar 624 and actuators 626a, 626b can have a variety of other configurations. For example, multiple EAP actuators in the form fiber bundles can extend laterally between an inner surface of the elongate shaft 612 and the slide bar 624. When energy is delivered to the actuators, the actuators can contract or shorten in length to pull the slide bar 624 toward the elongate shaft 612, thereby moving the slide bar 624 laterally. Alternatively, the slide bar 624 can be configured to move longitudinally to effect movement of the end effector 611, and the EAP actuator can be used to effect longitudinal movement of the slide bar 624. In other embodiments, the slide bar itself, or at least a portion of the slide bar, can be formed from an EAP actuator that is adapted to expand axially in a desired direction to move the slide bar laterally.

Figure 7A:
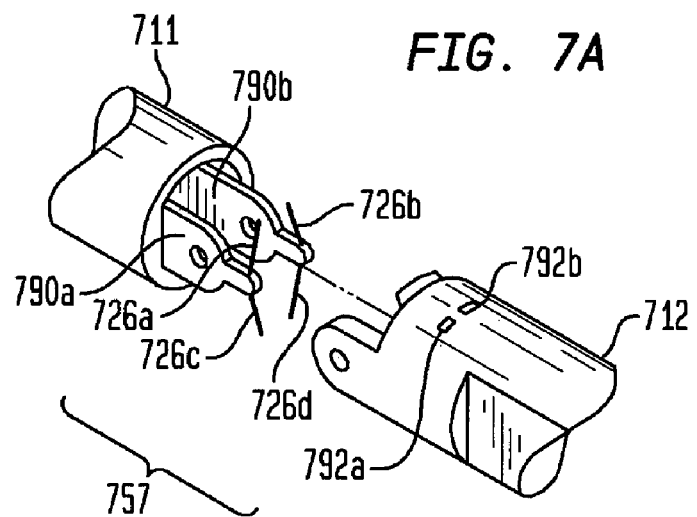
FIG. 7A is a partially exploded perspective view of another embodiment of an end effector movably coupled to a distal portion of an elongate shaft of a fastener delivery device, showing EAP actuators for articulating the end effector.
Figure 7B:
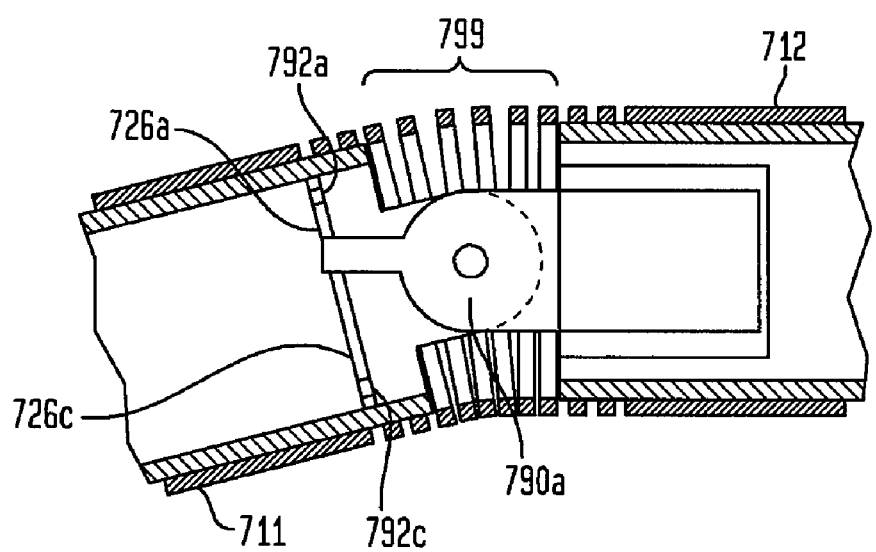
FIG. 7B is a partially cross-sectional view of the fastener delivery device shown in FIG. 7A, showing one of the EAP actuators electrically actuated to articulate the end effector.

FIGS. 7A-7B illustrate another embodiment of a technique for articulating a surgical fastening instrument. In this embodiment, the end effector 711 is pivotally coupled to the elongate shaft 712 by first and second opposed arms 790a, 790b coupled to opposed sides of the elongate shaft 712. First and third EAP actuators 726a, 726c are attached to and extend from opposed sides of a terminal end of the first arm 790a, and second and fourth EAP actuators 726b, 726d are attached to and extend from opposed sides of a terminal end of the second arm 790b. The distal end of each EAP actuator 726a-d is coupled to an inner sidewall of the elongate shaft 712 at an attachment point (first, second, and third attachment points 792a, 792b, 792c are shown). As a result, the first and second actuators 726a and 726b are attached to one side of the elongate shaft 712, and the third and fourth actuators 726c and 726d are attached to an opposite side of the elongate shaft 712. In use, energy can be delivered to the first and second EAP actuators 726a, 726b to cause the actuators 726a, 726b to axially contract or shorten, thereby pulling the first and second arms 790a, 790b in a lateral direction towards the first and second attachment points 792a, 792b. As a result, the end effector 711 is pivoted in a first direction. When energy delivery is terminated, the first and second actuators 726a, 726b will axially expand returning to their initial configuration, thereby moving the end effector 711 to its initial position in which it is longitudinally aligned with the elongate shaft 712. Energy can be delivered to the third and fourth actuators 726c, 726d to similarly move the end effector 711 in an opposite direction. As previously discussed, the amount of energy delivered can be controlled to control the amount of pivotal movement of the end effector 711. As shown in FIG. 7B, the device can also include a covering 799 surrounding at least a portion of the pivot frame assembly 757 to provide support thereto.

FIG. 8 illustrates yet another embodiment of a technique for articulating a surgical fastening instrument. In this embodiment, one or more actuating members can be incorporated into a pulley 898 that is part of a pivoting frame assembly 857. The pulley 898 can be made entirely of EAP actuators or, alternatively, EAP actuators can be attached to proximal and distal ends of the pulley 898. In the illustrated embodiment, first and second EAP actuators 826a, 826b are attached to the proximal and distal ends of the pulley 898. The EAP actuators 826a, 826b are anchored to the elongate shaft 812 to push and pull the end effector 811 to effect articulation. In particular, energy delivery to one of the EAP actuators, e.g., the first EAP actuator 826a, causes the first EAP actuator 826a to axially contract or shorten to move the pulley 898 in a first direction, thereby causing the end effector 811 to pivot in a first direction. Conversely, energy delivery to the second EAP actuator 826b causes the second EAP actuator to axially contract or shorten to move the pulley 898 in a second, opposite direction, thereby causing the end effector 811 to pivot in a second, opposite direction. Again, energy delivery can be controlled to control the amount of movement of the end effector 811.

Figure 9A:
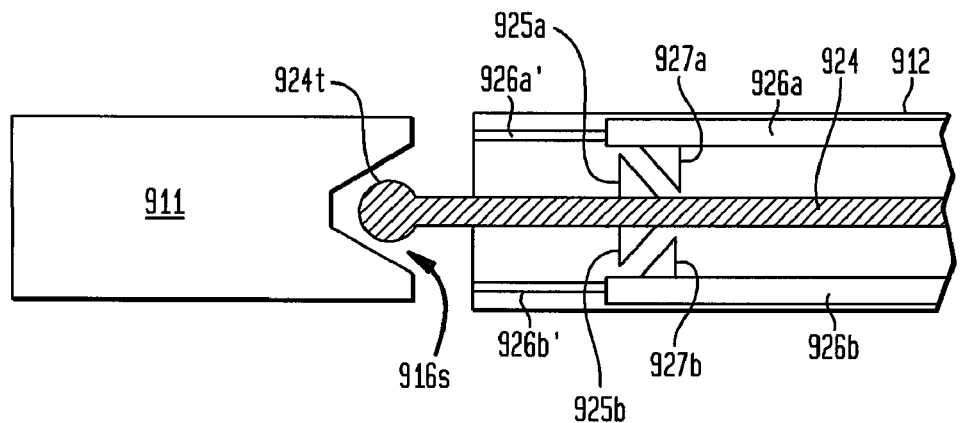
FIG. 9A is a partially cross-sectional view of another embodiment of an end effector movably coupled to a distal portion of an elongate shaft of a fastener delivery device, showing EAP actuators for articulating the end effector.
Figure 9B:
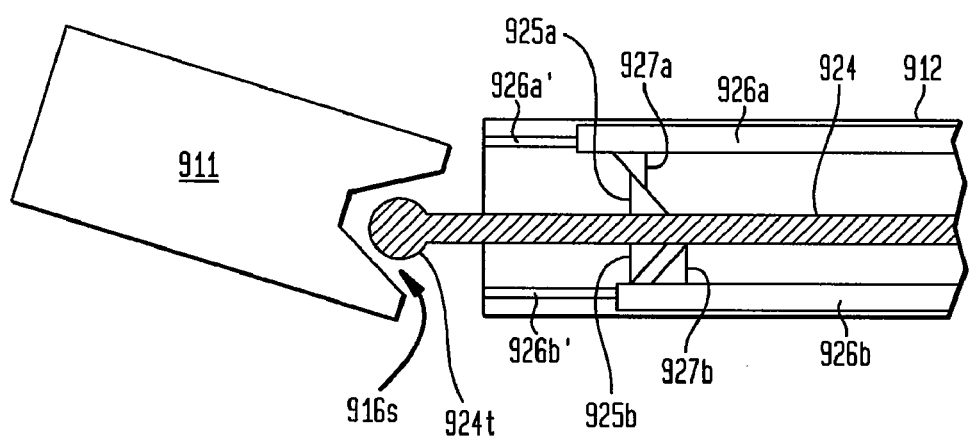
FIG. 9B is a partially cross-sectional view of the fastener delivery device shown in FIG. 9A, showing one of the EAP actuators electrically actuated to articulate the end effector.

FIGS. 9A-9B illustrate another embodiment of a technique for articulating an end effector relative to an elongate shaft of a surgical fastening instrument. In this embodiment, the elongate shaft 912 includes a slide bar 924 extending therethrough and having a ball 924t formed on a distal end thereof and received within a corresponding socket 916s formed in a proximal end of the end effector 911. The slide bar 924 also includes cam surfaces 925a, 925b formed thereon, preferably at a location proximal to the distal end of the elongate shaft 912. The cam surfaces 925a, 925b can have a variety of shapes and sizes, but in an exemplary embodiment, as shown, the cam surfaces 925a, 925b extend outward from opposed sides of the slide bar 924 and they are wedge-shaped members that increase in width in a proximal-to-distal direction. The device also includes first and second actuating members 926a, 926b extending through the elongate shaft 912 and positioned on opposed sides of the slide bar 924. Each actuating member 926a, 926b includes a cam surface 927a, 927b formed thereon and adapted to abut against the cam surfaces 925a, 925b formed on the slide bar 924. As a result, distal movement of the first actuating member 926a will cause the cam surface 927a formed thereon to slide against the cam surface 925a formed on the slide bar 924, thereby moving the slide bar 924 laterally away from the first actuating member 926a. As a result of the lateral movement of the slide bar 924, the ball 924t will cause the end effector 911 to pivot relative to the elongate shaft 912. Conversely, distal movement of the second actuating member 926b will cause the cam surface 927b formed thereon to slide against the cam surface 925b formed on the slide bar 924, thereby moving the slide bar 924 laterally away from the second actuating member 926b, and thus pivoting the end effector 911 in an opposite direction. A biasing element (not shown), such as a spring, can be disposed on each side of the slide bar 924 to bias the slide bar 924 to the central, resting position shown in FIG. 9A, thereby allowing the slide bar 924 to return to the resting position when the actuating members 926a, 926b are moving proximally.

In an exemplary embodiment, movement of each actuating member 926a, 926b can be achieved using an EAP actuator coupled thereto. As shown in FIGS. 9A and 9B, an EAP actuator cord 926a', 926b', preferably in the form of a fiber bundle type actuator, extends between a distal end of each actuating member 926a, 926b and a distal end of the shaft 912. When energy is selectively delivered to one of the EAP actuating cords, e.g., the first actuating cord 926a', the cord 926a' will axially contract or shorten, as shown in FIG. 9B, thereby pulling the actuating member 926a coupled to the actuated EAP cord 926a' in a distal direction. The cam surface 927a on the actuating member 926a will abut against the cam surface 925a on the slide bar 924 to move the slide bar 924 laterally toward the second actuating member 926b. As a result, the ball 924t on the distal end of the slide bar 924 will cause the end effector 911 to articulate or pivot thereabout.

A person skilled in the art will appreciate that the EAP actuators can have a variety of other configurations, and they can effect movement of the slide bar using a variety of other techniques. For example, rather than pulling the slide bar 924 distally when energy is delivered to the EAP actuating cords 926a', 926b', the EAP actuators can be coupled to a proximal end of the slide bar 924 and they can be adapted to push the slide bar 924 distally. In other embodiments, the cam surface 927a, 927b formed on each actuating member 926a, 926b can be formed from an EAP actuator such that energy delivery to the cam surface 927a, 927b causes the cam surface 927a, 927b to expand toward the slide bar 924, thereby moving the slide bar 924 in a desired direction to articulate the end effector 911. The amount of movement of each actuating member 926a, 926b, and thus the amount of articulation of the end effector, can also be controlled by controlling the amount of energy delivered to each EAP actuator.

Figure 10A:
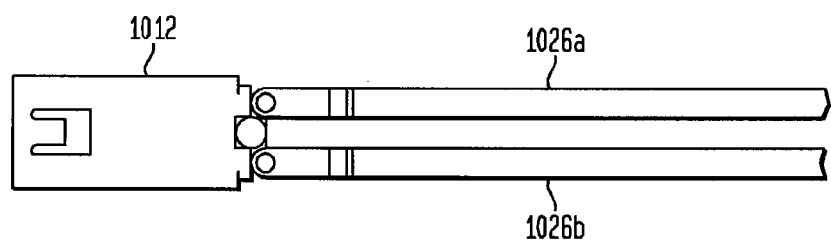
FIG. 10A is a partially cross-sectional view of yet another embodiment of an end effector movably coupled to a distal portion of an elongate shaft of a fastener delivery device, showing EAP actuators for articulating the staple applying assembly.
Figure 10B:
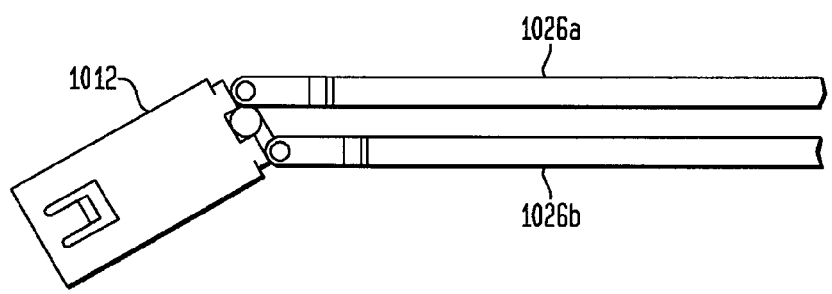
FIG. 10B is a partially cross-sectional view of the fastener delivery device shown in FIG. 10A, showing one of the EAP actuators electrically actuated to articulate the end effector.

FIGS. 10A-10B illustrate yet another embodiment of a technique for articulating an end effector 1012 of a surgical fastening instrument. In this embodiment, rather than using a slide bar to pivot the end effector 1012, two actuating members 1026a, 1026b are coupled directly to opposed sides of the end effector 1012 to push and pull the end effector 1012 to effect articulation. In particular, a distal end of each actuating member 1026a, 1026b is coupled to a proximal end of the end effector 1012 by a pivot joint, such that proximal movement of the first actuating member 1026*a* causes the end effector 1012 to pivot about the second actuating member 1026*b*, and proximal movement of the second actuating member 1026*b* causes the end effector 1012 to pivot about the first actuating member 1026*a*. The actuating members 1026*a*, 1026*b* can be moved using a variety of techniques. For example, all or a portion of each actuating member 1026*a*, 1026*b* can be formed from an EAP that is adapted to axially expand, or the actuating members 1026*a*, 1026*b* can be coupled to an EAP actuator for moving the actuating members 1026*a*, 1026*b* proximally and distally to articulate the end effector 1012.

Figure 11:
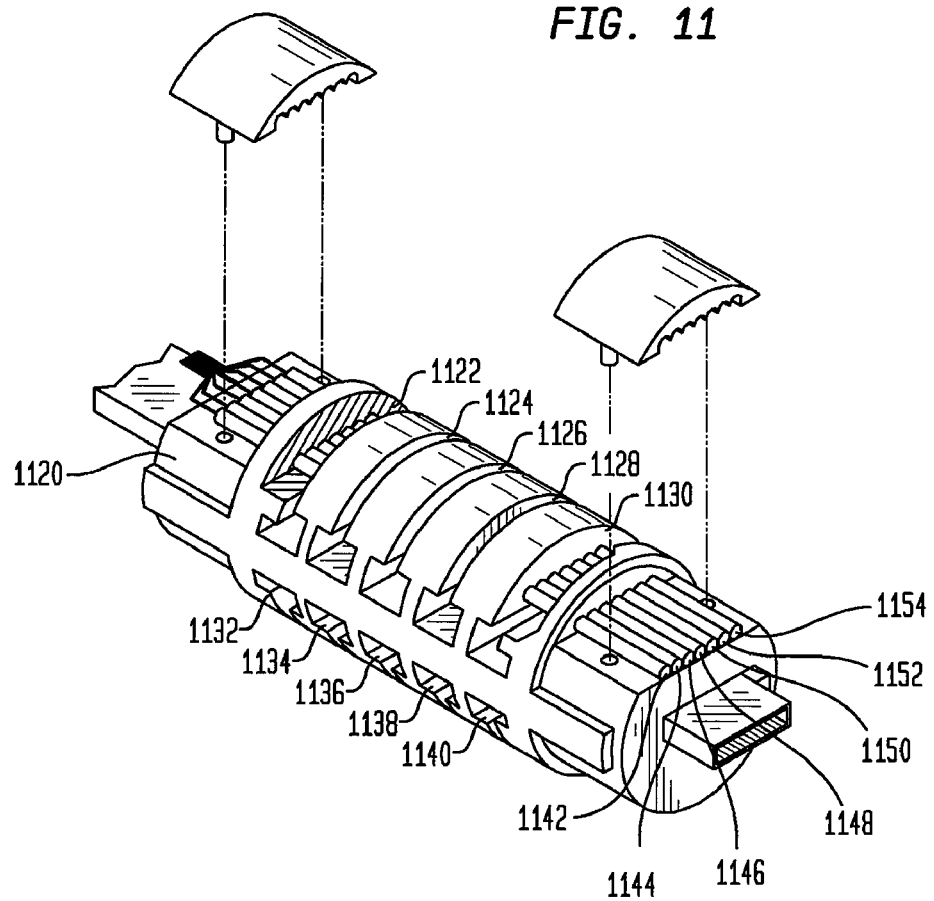
FIG. 11 is a perspective view of yet another embodiment of an end effector movably coupled by a flexible portion to a distal portion of an elongate shaft of a fastener delivery device, showing EAP actuators for articulating the end effector.

FIG. 11 illustrates another embodiment of a technique for articulating an end effector of a surgical fastening instrument. In this embodiment, the elongate shaft 1120 includes a flexible portion formed by a plurality of cut out portions 1122, 1124, 1126, 1128, 1130, 1132, 1134, 1136, 1138, 1140, 1142 (hereinafter 1122-1142) formed on opposed sides of the elongate shaft 1120. The cut out portions allow the elongate shaft 1120 to flex thereabout. One or more actuators can be positioned relative to the cut out portions to effect pivotal or bending movement of an end effector (not shown) relative to the elongate shaft 1120. FIG. 11 illustrates multiple EAP actuator cords 1144, 1146, 1148, 1150, 1152, 1154 (hereinafter 1144-1154) extending longitudinally through the elongate shaft 1120 where the cut out portions are formed. The EAP actuator cords 1144-1154 extend longitudinally parallel to one another, and they are coupled to the elongate shaft 1120 at a first end just proximal to the cut out portions 1122-1142 and at a second end just distal to the cut out portions 1122-1142. In use, energy can be selectively delivered to any one or combination of the EAP actuator cords 1144-1154 to flex the cut out portions 1122-1142 and thereby articulate the end effector in a desired direction. For example, energy can be delivered to the first EAP actuator cord 1144 to cause the first actuator cord 1144 to axially contract or shorten, thereby pulling the opposed ends of the cord 1144 toward one another. Since the ends of the first actuator cord 1144 are attached to the elongate shaft 1120 at opposed ends of the cut out portions, and since the first EAP actuator cord 1144 is offset from a central axis of the elongate shaft 1120, the first EAP actuator cord 1144 will cause the elongate shaft 1120 to bend in a first direction. Accordingly, one or more actuator cords 1144-1154 can be selectively activated, i.e., energy can be selectively delivered thereto, to effect movement of the end effector in a desired direction. A person skilled in the art will appreciate that a variety of other techniques can be used to cause the cut out portions to bend.

In other embodiments, one or more EAP actuators can be positioned within, on, or around the flexible portion of the elongate shaft at various locations, and the EAP actuators can be configured to flex the flexible portion when energy is delivered to the actuators, thereby articulating the end effector. For example, multiple EAP actuators can extend axially along distinct portions of a flexible portion of an elongate shaft, or they can be positioned at various other locations around the circumference of the flexible portion. In use, energy delivery to a first actuator, for example, to cause the first actuator to axially contract thereby bending a portion of the flexible portion. A user can thus selectively deliver energy to one or more actuators to articulate and position the end effector as desired.

A person skilled in the art will appreciate that any of the above embodiments can include a locking feature that allows the device to maintain its articulated position when energy delivery is terminated to the EAP actuators. In particular, when energy delivery is terminated the EAP actuator(s) axially expands to return the end effector to its initial position in which it is longitudinally aligned with the elongate shaft. A locking mechanism can thus be used to lock the end effector in a desired articulated position prior to terminating energy delivery to the EAP actuators.

Figure 12A:
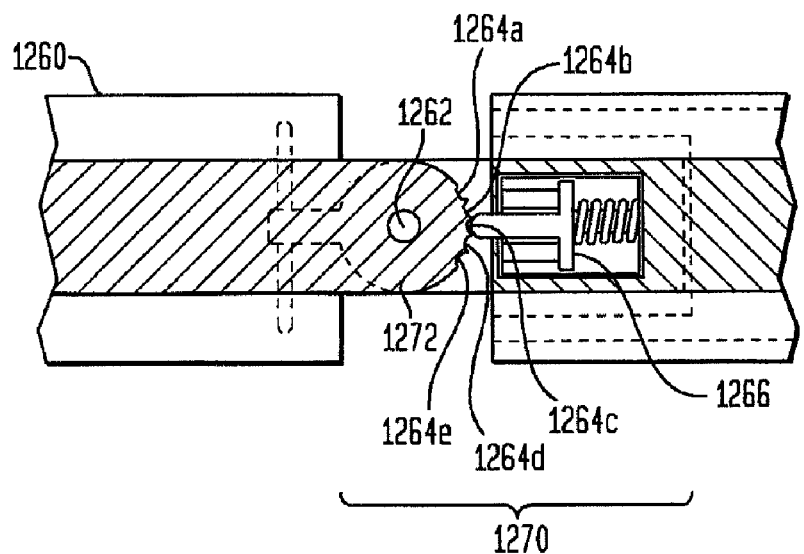
FIG. 12A is a perspective view of one exemplary embodiment of a locking mechanism in an unactivated position for locking a movable joint between an end effector and an elongate shaft of a fastener delivery device.
Figure 12B:
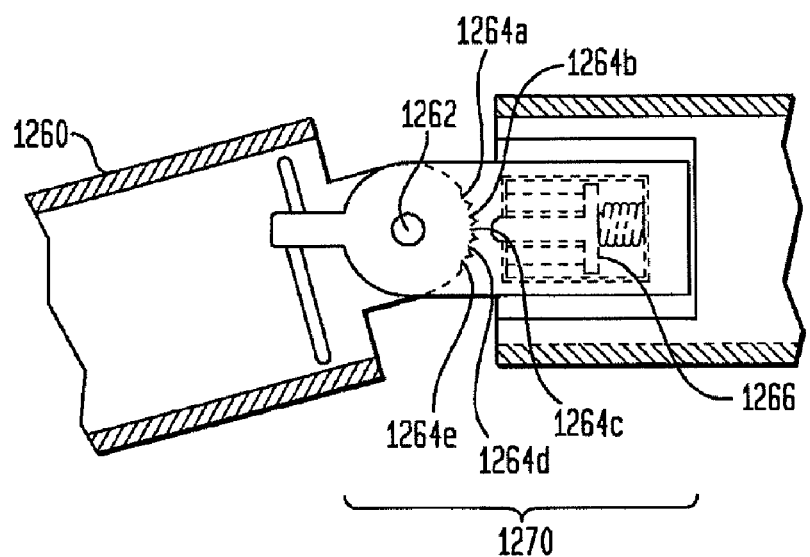
FIG. 12B is a perspective view of the locking mechanism of FIG. 12A activated to lock the movable joint in a fixed position.

While the locking mechanism can have a variety of configurations, FIGS. 12A-12B illustrate one exemplary embodiment of an articulation lock 1270 that is incorporated into a pivoting articulation joint 1262. As shown, the articulation joint 1262 includes a rotary structure 1272 having a plurality of holes 1264*a*, 1264*b*, 1264*c*, 1264*d*, 1264*e* that are adapted to receive a plunger to prevent rotational movement of the articulation joint 1262. A stop, which in one embodiment can be a spring loaded plunger 1266, is formed within the elongate shaft of the device and located proximal to the rotary structure 1272. The plunger 1266 is also coupled to an EAP actuator (not shown) that, when actuated with energy, effects movement of the plunger 1266 thereby allowing the articulation joint 1262 to move. In particular, as shown in FIG. 12A, when the device is in an un-actuated position, the plunger 66 rests in one of the holes (hole 64*e* as shown) of the rotary structure 1272, thereby maintaining the end effector in a fixed position. Energy delivery to the EAP actuator, as shown in FIG. 12B, will pull the plunger 1266 out of the hole 1264*e* to allow the articulation joint 1262 to move to a desired position. The various techniques previously described can be used to articulate the end effector. Once the end effector is moved to a desired articulated position, the EAP actuator can be de-actuated, i.e., energy delivery can be terminated, allowing the spring to bias the plunger 1266 into one of the holes of the rotary structure 1272. The end effector is thereby again maintained in a fixed position. One skilled in the art will appreciate that a variety of other locking mechanism can be incorporated into an articulating joints, such as a ratchet and teeth system.

A person skilled in the art will appreciate that the EAP actuators can have a variety of other configurations to effective movement of the plunger. For example, in another embodiment an EAP actuator can replace the plunger and can be directly connected to a driver to move the driver distally through the elongate shaft. One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical fastener delivery device, comprising:
    an elongate shaft defining a longitudinal axis;
    an end effector movably coupled to the elongate shaft by an articulation joint, the end effector being configured to sequentially deliver a plurality of fasteners to tissue; and
    an electroactive polymer actuator disposed within the elongate shaft and expandable in a direction orthogonal to the longitudinal axis of the elongate shaft when energy is delivered to the electroactive polymer actuator and configured to thereby move the end effector about the articulation joint relative to the elongate shaft.

2. The device of claim 1, wherein the elongate shaft includes a slide bar extending therethrough and having a distal end coupled to the articulation joint, the electroactive polymer actuator being configured to move the slide bar in a direction orthogonal to the longitudinal axis of the device to effect movement of the end effector.

3. The device of claim 2, wherein the electroactive polymer actuator comprises first and second electroactive polymer actuators disposed on opposed sides of the slide bar.

4. The device of claim 2, wherein the slide bar includes gears formed on a distal end thereof and adapted to engage corresponding gears formed in the articulation joint.

5. The device of claim 1, wherein the articulation joint comprises a pivot joint, and the electroactive polymer actuator comprises a first electroactive polymer actuator extending between a first side of the end effector and a first side of the elongate shaft, and a second electroactive polymer actuator extending between a second opposed side of the end effector and a second opposed side of the elongate shaft.

6. The device of claim 1, wherein the articulation joint comprises a flexible portion formed between the elongate shaft and the end effector.

7. The device of claim 6, wherein the electroactive polymer actuator comprises a plurality of electroactive polymer actuators coupled to the flexible portion at distinct locations, each of the plurality of electroactive polymer actuators being configured to change orientations when energy is selectively delivered thereto to flex the flexible portion.

8. The device of claim 1, further comprising a fastener advancing assembly disposed through the elongate shaft and adapted to sequentially advance a plurality of fasteners into the end effector.

9. The device of claim 1, wherein the end effector includes opposed jaws adapted to receive a fastener in the form of a clip therebetween.

10. The device of claim 1, wherein the end effector comprises a stapling mechanism for stapling tissue.

* * * * *